(12) United States Patent
Belbruno

(10) Patent No.: US 11,326,197 B2
(45) Date of Patent: May 10, 2022

(54) MOLECULARLY IMPRINTED POLYMER-BASED PASSIVE SENSOR

(71) Applicant: FRESHAIR SENSOR, LLC, Hanover, NH (US)

(72) Inventor: Joseph James Belbruno, Hanover, NH (US)

(73) Assignee: FRESHAIR SENSOR, LLC, Hanover, NH (US)

( * ) Notice: Subject to any disclaimer, the term of this patent is extended or adjusted under 35 U.S.C. 154(b) by 1457 days.

(21) Appl. No.: 14/065,990

(22) Filed: Oct. 29, 2013

(65) Prior Publication Data

US 2014/0242601 A1 Aug. 28, 2014

Related U.S. Application Data

(60) Provisional application No. 61/719,580, filed on Oct. 29, 2012.

(51) Int. Cl.
| | |
|---|---|
| *C12Q 1/04* | (2006.01) |
| *G01N 33/543* | (2006.01) |
| *B01J 20/32* | (2006.01) |
| *B01J 20/28* | (2006.01) |
| *B01J 20/26* | (2006.01) |

(52) U.S. Cl.
CPC .............. *C12Q 1/04* (2013.01); *B01J 20/264* (2013.01); *B01J 20/268* (2013.01); *B01J 20/28033* (2013.01); *B01J 20/3268* (2013.01); *G01N 33/54386* (2013.01); *B01J 2220/66* (2013.01); *G01N 2600/00* (2013.01)

(58) Field of Classification Search
None
See application file for complete search history.

(56) References Cited

U.S. PATENT DOCUMENTS

| | | | |
|---|---|---|---|
| 4,314,027 A | 2/1982 | Stahr | |
| 5,110,833 A * | 5/1992 | Mosbach | ............... B01J 20/268 |
| | | | 435/183 |
| 5,212,061 A * | 5/1993 | Snyder | ............. G01N 33/56955 |
| | | | 435/21 |

(Continued)

FOREIGN PATENT DOCUMENTS

| | | |
|---|---|---|
| WO | WO 2008/045596 | 4/2008 |
| WO | WO 2011/058308 | 5/2011 |

(Continued)

OTHER PUBLICATIONS

Blanco-Lopez, M.C., Gutierrez-Fernandez, S., Lobo-Castanon, M.J., Miranda-Ordieres, A.J., Tunon-Blanco, P. "Electrochemical sensing with electrodes modified with molecularly imprinted polymer films". Anal. Bioanal. Chem. (2004) 378:1922-1928.*

(Continued)

*Primary Examiner* — Anish P Desai
*Assistant Examiner* — Thomas A Mangohig
(74) *Attorney, Agent, or Firm* — Lathrop GPM LLP

(57) ABSTRACT

Systems and methods for the detection of one or more target molecules emitted from microbial sources are described. The systems and methods may include a molecularly imprinted polymer film; a strain sensitive surface, wherein the molecularly imprinted polymer film comprises a polymer host with one or more binding sites for one or more target molecules. The molecularly imprinted polymer film may be coated upon the strain sensitive surface.

29 Claims, 4 Drawing Sheets

(56) References Cited

U.S. PATENT DOCUMENTS

| | | |
|---|---|---|
| 6,484,560 B1 | 11/2002 | Prest |
| 6,787,350 B2 | 9/2004 | Bigelow, Jr. |
| 6,798,220 B1 | 9/2004 | Flanigan et al. |
| 7,291,465 B2 | 11/2007 | Karaolis |
| 2003/0129618 A1 | 7/2003 | Moronne et al. |
| 2005/0035868 A1* | 2/2005 | Back .............. G08B 17/113 340/627 |
| 2006/0041057 A1* | 2/2006 | Koecher ........... C08G 18/4841 525/50 |
| 2006/0041099 A1* | 2/2006 | Cernohous ........ C08G 18/0814 528/44 |
| 2008/0286830 A1 | 11/2008 | Scotter et al. |
| 2009/0325147 A1 | 12/2009 | Jones, Jr. |
| 2010/0039124 A1* | 2/2010 | Belbruno .............. B82Y 15/00 324/693 |
| 2010/0068820 A1 | 3/2010 | Meathrel et al. |
| 2010/0107740 A1* | 5/2010 | Moularat ................ C12Q 1/04 73/31.03 |
| 2010/0311181 A1 | 12/2010 | Abraham et al. |
| 2011/0054132 A1 | 3/2011 | Yiannikouris et al. |
| 2011/0143962 A1 | 6/2011 | Chaubron |
| 2015/0241374 A1 | 8/2015 | Belbruno |

FOREIGN PATENT DOCUMENTS

| | | |
|---|---|---|
| WO | WO-2011/058308 | 5/2011 |
| WO | WO 2014/070727 | 5/2014 |
| WO | WO-2014/070727 | 5/2014 |
| WO | WO 2015/130529 | 9/2015 |

OTHER PUBLICATIONS

International Search Report and Written Opinion in corresponding International Application No. PCT/US2015/016373, dated Jul. 21, 2015, 10 pages.

U.S. Appl. No. 14/624,813, filed Feb. 18, 2015, Belbruno.

Fu et al., Quartz Crystal Microbalance Sensor for Organic Vapor Detection Based on Molecularly Imprinted Polymers,: Anal. Chem., 2003: 75, pp. 5387-5393.

International Search Report and Written Opinion in corresponding International Application No. PCT/US2013/067246, dated Mar. 20, 2014, 12 pages.

Meruva et al., "Rapid identification of microbial VOCs from tobacco molds using closed-loop stripping and gas chromatography/time-of-flight mass spectrometry," J Ind Microbiol Biotechnol, 2004: 31, pp. 482-488.

Moularat et al., "Detection of fungal development in closed spaces through the determination of specific chemical targets," Chemosphere 72, 2008, pp. 224-232.

Yoon et al., "Colorimetric Sensors for Volatile Organic Compounds (VOCs) Based on Conjugated Polymer-Embedded Electrospun Fibers," J. Am. Chem. Soc. 2007: 129, pp. 3038-3039.

* cited by examiner

MOLECULARLY IMPRINTED POLYMER-BASED PASSIVE SENSOR

CROSS REFERENCE TO RELATED APPLICATIONS

The present application claims priority to U.S. Provisional Patent Application No. 61/719,580, filed Oct. 29, 2012; the content of which are incorporated herein in its entirety.

FIELD OF THE INVENTION

The present invention relates to systems and methods for passive sensors, and, more specifically, to systems and methods for molecularly imprinted polymer-based sensors for detecting target molecules, for example, from microbial sources.

BACKGROUND OF THE INVENTION

Molecular imprinting is a technique to produce molecule specific receptors analogous to those receptor binding sites in biochemical systems. A molecularly imprinted polymer (MIP) is a polymer that is formed in the presence of a template or target analyte molecule producing a complementary cavity that is left behind in the MIP when the template is removed. The MIP demonstrates affinity for the original template molecule over other related and analogous molecules.

Mold growth in indoor environments is a serious safety concern. The obvious disruption of everyday living and the often serious public health issues associated with mold growth are well-known. Current sampling for the presence of mold presents challenges both in terms of effectiveness and financial costs, providing the impetus for a new screening method. Microbes are known to release microbial volatile organic compounds (mVOCs) during their growth. The grouping of common mVOCs contains approximately nineteen small molecules. While some microbes may release other molecules that are more specific to the microbe, a consensus generally exists for common mVOCs detected in dwellings. For example, four and eight carbon molecules, such as 1-octen-3-ol and 2-butanol, as well as ring systems, including 2-methylfuran, 3-methylfuran and anisole, have been consistently reported in relation to mold growth. These molecules are identified as markers of microbial activity and shown to be independent of the growth medium for the microbes. Testing for a profile of selected marker molecules may provide an early warning of the growth of mold in, for example, a dwelling.

Sensors for the detection of mold, especially in the early stages of development when it is considered most important to halt mold progression, require laboratory measurements. For example, existing sensing systems require pumps to draw air through a tube, followed by complex analysis after adsorption of the mold marker molecules onto a solid phase adsorbent. Furthermore, this type of sensor is not specific for a single airborne marker, typically adsorbing all volatile organic compounds (VOCs) and requiring a sophisticated analytical method to identify the presence of mold in, for example, a household. The sensors available are not real-time, and only provide an indication of toxic levels in a post-exposure mode.

SUMMARY OF THE INVENTION

Embodiments of the present invention solve many of the problems and/or overcome many of the drawbacks and disadvantages of the prior art by providing systems and methods for molecularly imprinted polymer-based sensors.

This disclosure relates to the field of molecularly imprinted polymers (MIP), and in certain embodiments relates to passive sensors based on MIP films to simultaneously detect mVOCs specifically emitted by growing mold colonies.

MIPs disclosed herein may be used for sensing. Polymers employed in the production of MIPs disclosed herein are also referred to as polymer hosts. Molecules disclosed herein for the production of the cavities in the MIPs are referred to interchangeably as templates, targets, or target molecules.

Embodiments described herein may provide systems and methods to produce sensors that incorporate a strain sensitive MIP film. The methods may involve using the target molecules in the preparation of the MIP films and sensors comprising MIP films. When the target molecule is removed, it may leave behind a MIP with cavities complementary in shape and functionality to the target molecule, which can rebind, in the cavities, a target identical to the original target molecule.

Certain non-limiting embodiments of the MIP sensors provided for herein may have strain sensitive elements incorporating thin polydiacetylene (PDA) films prepared by spin-casting or other techniques known in the art. Certain non-limiting embodiments of the MIP sensors may be for microbial VOC detection via changes in the color of the MIP upon adsorption of, for example, 2-methylfuran. Other changes may also signal adsorption of target molecules. Significant increases in the strain within these MIP sensor films may occur upon exposure to the microbial VOC vapors against which they were templated. The films disclosed herein may be responsive to some other volatile organics, but the response of the films to non-target molecules may be significantly reduced. Significant changes, such as in the color, of the imprinted films may occur when exposed to a target molecule as compared to control films involving coating with unimprinted polymer. A complete sensor may include a set of MIPs templated to a plurality, such as five or more, different microbial VOC emissions.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE PREFERRED EMBODIMENTS

Figure 1:
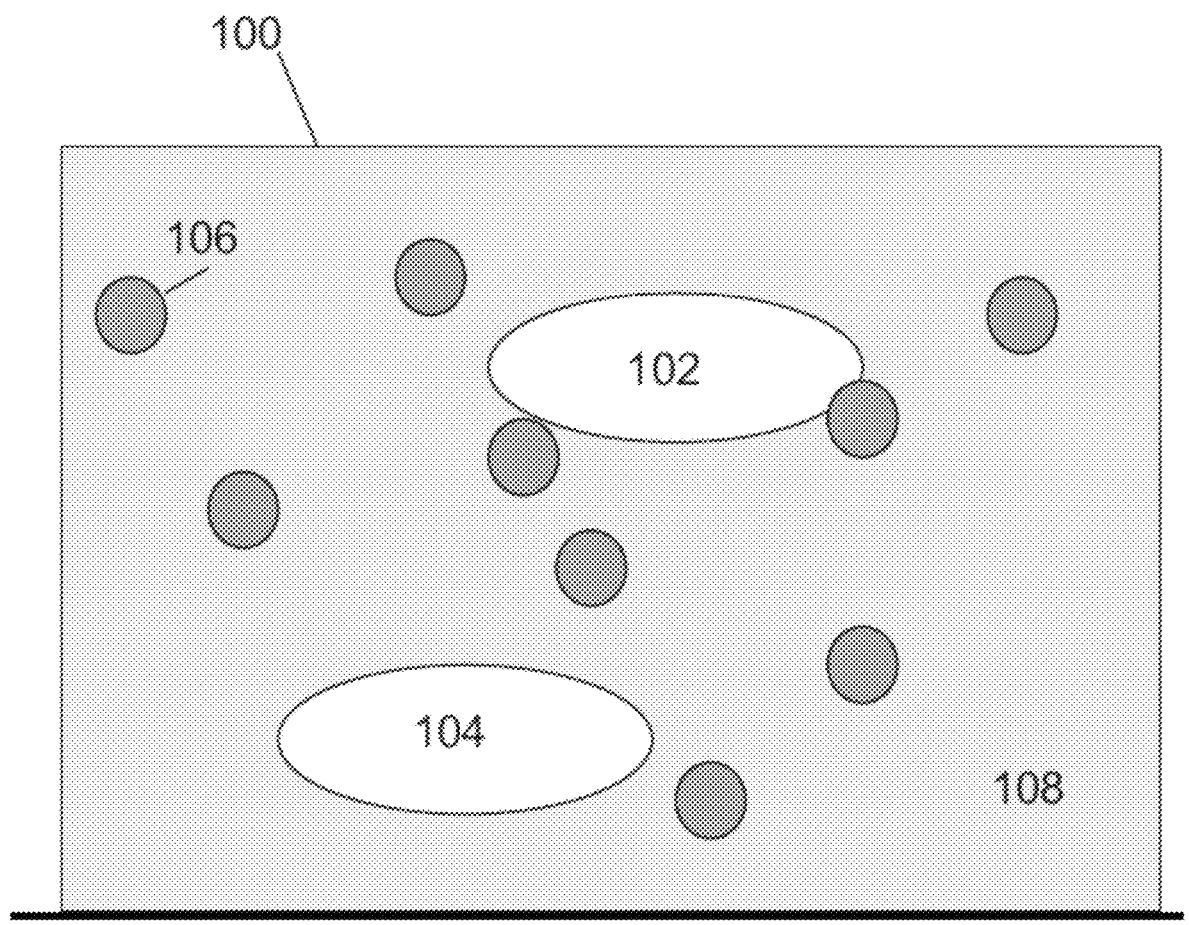
FIG. 1 shows an exemplary, simplified molecularly imprinted polymer solution prior to film deposition according to one embodiment.

Systems and methods are described for molecularly imprinted polymer-based sensors. In certain embodiments, the tools and procedures may be used in conjunction with detection of microbial volatile organic compounds (mVOCs). The examples described herein relate to mold detection for illustrative purposes only. The systems and methods described herein may be used for many different industries and purposes, including detection of any microbial growth, detection of various volatile organic compounds, detection of other classes of molecules, and/or other industries completely. In particular, the systems and methods may be used for any industry or purpose where molecularly imprinted polymer-based sensors are needed.

Molecularly Imprinted Polymer (MIP) Films and Sensors

Embodiments described herein may provide systems and methods for producing MIPs. The polymer of a MIP may contain one or more binding sites for one or more target molecules. Without being bound by any particular theory, it is believed that the target molecule may bind to the binding sites in the polymer layer via physical or chemical forces such as electrostatic interactions, van der Waals forces, ionic bonds or even covalent bonds. The polymer layer of the MIP may also be referred to as the polymer host. The polymer layer (polymer host) of the MIP may contain a structural polymer component (structural component) and a reporting polymer component (reporting component). The structural component of the polymer layer may provide structural support for the polymer layer of the MIP. In certain embodiments, the structural component primarily forms the binding site of the polymer host. In certain embodiments, the reporting component of the polymer host is a strain sensitive polymer that allows for detection of rebinding.

In certain embodiments, a change in a physical property associated of the polymer host may indicate the presence of a target molecule in a MIP film. The absence of a change may indicate the absence of a target molecule in a MIP film. In certain embodiments, a change in strain of the polymer host may indicate presence of a target molecule. The change may be an alteration in any measurable property of the polymer host. In certain embodiments, the change may be a change in color. In alternate embodiments, the change may be a change in electrical resistance or conductivity. The MIP may be coated onto an electrode and a change in the resistance of the polymer between the adsorbed and desorbed state may be used to detect mVOCs. Alternatively, a capacitor may be constructed with the MIP as a dielectric between two electrodes. In certain embodiments, the bottom electrode may be solid, the MIP may be a next layer, and then an electrode may be adjacent the MIP, where the electrode that has one or more gaps that may allow vapor to pass through. Changes in capacitance in the presence and absence of target mVOCs may be measured.

As used herein, a film generally refers to a coating of a surface. In alternate embodiments, a film may be a thin layer of material that is not coated on another surface. An embodiment of a film may be coating of a surface by a polymer or MIP. In one embodiment, a MIP film may be from about 1 nm to about 100 µm in thickness. In certain embodiments, the MIP film may be from about 100 nm to about 500 nm in thickness. Preferably, the MIP film may allow the changes in adsorption to influence the strain sensitive layer and report an outcome. In general, MIP film sensor functionality may depend upon detecting differences in a property of the MIP film, such as color of the MIP film, as a function of the adsorption of a target molecule. In certain embodiments, MIP film sensors can be tested for their ability to detect mVOCs by using various vapor chambers or otherwise exposing the MIP film sensors disclosed herein to samples of various gases.

MIP strain sensitive polymers (reporting components) may include, but are not limited to, polydiacetylene (PDA) and similar compounds. MIP structural polymers may include, but are not limited to, poly(4-vinylphenol), polyurethane, nylons, poly(4-vinylpyridine), polyvinylpyrrolidinone (PVPy), polyethyleneimine (PEI), polystyrene, and combinations thereof. Depending upon the MIP polymers of choice, the solvents in which the MIPs have high solubility can include, but are not limited to, alcohols, dimethylformamide, water, formic acid, chloroform, and combinations thereof. It will be appreciated by those skilled in the art that modification of polymers and/or solvents may allow for tuning the process of producing MIPs to the chemistry of a target molecule.

In certain embodiments, target molecules may include mVOCs that are emitted during mold growth. Examples of target molecules may include, but are not limited to, 1,3-octadiene, 1-octen-3-ol, 2-butanol, 2-methylfuran, 3-methylfuran, anisole, and combinations thereof.

In some embodiments of the MIPs disclosed herein, homologous molecules, homologs, of the target molecule can be used instead of the target molecule to produce MIPs that detect the target molecule. Homologs of target molecules may include molecules that are similar to the target molecule in various attributes including, but not limited to, size, electrostatic potentials, electronegativity, charge density, chemical bonding potential, and molecules that have similar shapes to the target molecule. Homologs may include isomers and stereoisomers of the target molecule.

In an embodiment, MIP films can be regenerated by extracting and/or evaporating target molecules from a MIP film by soaking or washing in a solvent in which the polymer host is insoluble, but the target molecule is soluble. In an embodiment, the target molecules can be removed from the MIP binding sites through extraction and/or evaporation processes. The MIP films may then be washed and dried to allow the solvent and the target molecule to be separated from the MIP films. After extraction and/or evaporation of the target molecule, the MIP films may be ready to detect target molecules again. If the mVOCs of interest are charged, the films may be regenerated by charging or reversing the charge on the MIP film.

Strain measurements, such as color changes, of embodiments of the sensors presented herein may be indicative of the binding of template molecules. Additional evidence of target molecules being bound in the MIP layer can be obtained through IR spectroscopy and gas chromatographic experiments.

The morphology of MIP films disclosed herein can be further characterized by scanning electron microscopy.

Methods of Making MIP Films and Sensors

Systems and methods are described for making MIPs and sensors that use MIPs. In an embodiment, MIPs may be made by mixing together a structural component, a reporting component, a target molecule and a first solvent. In an embodiment, a structural component may be a structural polymer. In an embodiment, a reporting component may be a reporting polymer. In an embodiment, the solution of the polymer components, the first solvent, and the target molecule may be a molecularly imprinted polymer solution. The molecularly imprinted polymer solution can then be coated onto a surface and allowed to dry. When the molecularly imprinted polymer solution is drying, the polymers may form the binding sites for the dissolved target molecules as the polymer layer polymerizes around the target molecules. Next, the target molecule may be selectively removed from the MIP layer by either evaporation of the target molecule or through extraction with a solvent that selectively dissolves the target molecule, but does not dissolve the polymer host.

The solvent used in making the MIPs can boil at a lower temperature than the target molecule. This may allow the template to form recognition sites during spin or dip coating. A solvent can then be used to remove the template. The solvent should be incompatible with the polymer host to promote precipitation of the MIP. Alternatively, the volatile organic molecule or template can be evaporated from the MIP if the solvent has a lower boiling point than the target.

There are various techniques for depositing films including electropolymerisation, spin casting and laser deposition. In certain embodiments of the present disclosure, polydiacetylene (PDA) may be employed to directly measure the target concentration in concert with a second polymer included in composite materials to improve the porosity of the film. In certain embodiments, polyethyleneimine (PEI) and polyimide resin may increase porosity. PDA may change color from blue to red when it is subjected to increased strain due to, for example, the binding of the target molecule.

In an embodiment, the sensor may be a device that simultaneously monitors a plurality of the mVOCs. In certain embodiments, the device may simultaneously any combination of various mVOCs. In a preferred embodiment, the device may simultaneously monitor at least five of the mVOCs. Simultaneous detection may significantly reduce false positive signals. In an embodiment, the sensor may be read visually. In another embodiment, the sensor may be coupled to electronics that read the MIPs and report wirelessly to a central facility. Alternatively, the sensor may be incorporated into a portable and/or handheld device for measurement and processing onsite. The polymer host and the MIP synthesis for each component may determined by the physical and/or chemical characteristics of the targeted mVOCs. Each MIP within a test strip may be specific to a single target molecule. In an embodiment, the colorimetric reporting aspect of the sensors may be based on a stress induced polymer color change from blue to red upon reinsertion of the template into the MIP.

The structural polymer may be based on hydrogen-bonding interactions. The structural polymer may include, but is not limited to, poly(4-vinylphenol), polyurethane, nylons, poly(4-vinylpyridine), polyvinylpyrrolidinone, polyethyleneimine, polystyrene, and combinations thereof. Other structural polymers may be used. MIP production is typically, but not limited to, a ratio of approximately 1 g of structural polymer dissolved in approximately 10 mL of solvent with approximately 0.3 g of the target molecule. Target molecule can range from about 1 to about 10%, preferably in the range from about 3 to about 5%. In certain embodiments, the polymer is not greater than about 10% and may be between about 3 to about 10%. The mixture may be precipitated to produce the solid MIP. Precipitation may include spin coating or drop casting or formation of nano- or microspheres. The MIP solution may be coated onto the prepared polydiacetylene (PDA) reporting structure.

The reporting layer of the sensor, such as the color reporting PDA, may be produced by any standard polymerization methods known to one of skill in the art. In an embodiment, the production may be started with a diacetylene monomer, for example 10,12-pentacosadienoic acid. A solution made with a ratio of approximately 100 mg in approximately 5 mL of solvent may be sonicated and stirred. This polymerization solution may be deposited into the membrane test strip and irradiated at approximately 254 nm for approximately 5 minutes. The MIP may then be applied to this polymerized reporting layer. The MIP could also be formed to incorporate antibodies to molecules that could then be used to detect the antigen that bound to the antibody. Similarly, the MIP could incorporate antigens to permit them to detect antibodies or antibody conjugates.

Embodiments of MIP Films and Sensors

FIG. 1 illustrates an embodiment of a simplified molecularly imprinted polymer solution. A molecularly imprinted polymer solution 100 may include structural components 102, 104 dissolved in a solvent 108. The polymer solution 100 may also include one or more target molecules 106 dissolved in the solvent 108. As illustrated in FIG. 1, a target molecule 106 may be bonded to the structural component 102 in the polymer solution 100, also referred to as the MIP solution.

The interaction between a polymer host and a target molecule in a MIP can involve non-covalent bonding, such as hydrogen bonding, between the polymer host and the target molecule. The binding interaction can exploit other electrostatic forces in conjunction with shape recognition, but the interaction between polymer host and the target molecule is not limited to non-covalent forces and can also include ionic and/or covalent chemical bonds between the target molecule and the polymer host.

When the target molecule is removed via extraction or evaporation or by other removal means, it may leave behind a MIP with cavities that are complementary in shape to the target molecule and act as a binding site to the target molecule or similar molecules. The MIP films disclosed herein may be capable of rebinding target molecules through subsequent rounds of use when the MIP is regenerated between measurements by removing the target molecule from the MIP before the next use of the MIP film and/or sensor.

In another embodiment, MIPs can be produced by dissolving the polymer or polymer host components, i.e., reporting and structural, and target molecules in a first solvent to form a molecularly imprinted polymer solution. In one embodiment, the target molecule may form between about 1 and about 30 weight percent of the molecularly imprinted polymer solution. In a preferred embodiment, the target molecule forms between about 2 and about 20 weight percent of the molecularly imprinted polymer solution. In a more preferred embodiment, the target molecule forms between about 2 and about 15 weight percent of the molecularly imprinted polymer solution.

In an embodiment of a MIP of the present disclosure, the molecularly imprinted polymer solution has a molar ratio of from about 10:1 to about 1:1 to about 1:10 of the structural component to the reporting component. In an embodiment, the molecularly imprinted polymer solution is from about 1 to about 30 percent of the target molecule or homolog by weight. In a preferred embodiment of a MIP of the present disclosure, the molecularly imprinted polymer solution may have a molar ratio of from about 5:1 to about 1:1 to about 1:5 of the structural component to the reporting component. In a preferred embodiment, the molecularly imprinted polymer solution is from about 2 to about 20 percent of the target molecule or homolog by weight. In a more preferred embodiment of a MIP of the present disclosure, the molecularly imprinted polymer solution may have a molar ratio of from about 1:1 of the structural component to the reporting component. In a more preferred embodiment, the molecularly imprinted polymer solution is from about 2 to about 10 percent of the target molecule or homolog by weight.

In an embodiment of a MIP of the present disclosure, polymethylmethacrylate is used as the structural component and polydiacetylene is used as the reporting component for the polymer host of a MIP film having 3-methylfuran as the target molecule.

The first solvent should be suitable for each component of the polymer host and the target molecule. For example, polymethylmethacrylate and 3-methylfuran are soluble in dimethylformamide. The polymer hosts and solvents can vary for a particular target molecule of interest. Non-limiting examples of solvents can include alcohols, dimethylformamide, water, formic acid and chloroform.

In an embodiment, after dissolving the polymer host components, 2 to 10 weight percent of the target molecule may be added in the polymer solution, followed by stirring for about 20 hours to uniformly mix the target molecule in the polymer solution and form the molecularly imprinted polymer solution. Stirring times can vary depending on the system, including components such as polymer host and target. Generally, stirring times may range from approximately 5 hours to approximately 24 hours. Other stirring times may be used. In general, when a higher target concentration is used, the sensitivity of the MIP to target detection may increase. However, the MIP's detection or separation for a particular molecule or molecular specificity may be reduced.

In an embodiment, thin films are produced by drop casting onto plastic substrates and allowed to air dry for about 1 hour. The final film can be stored until needed for use to rebind the target.

Figure 2A:
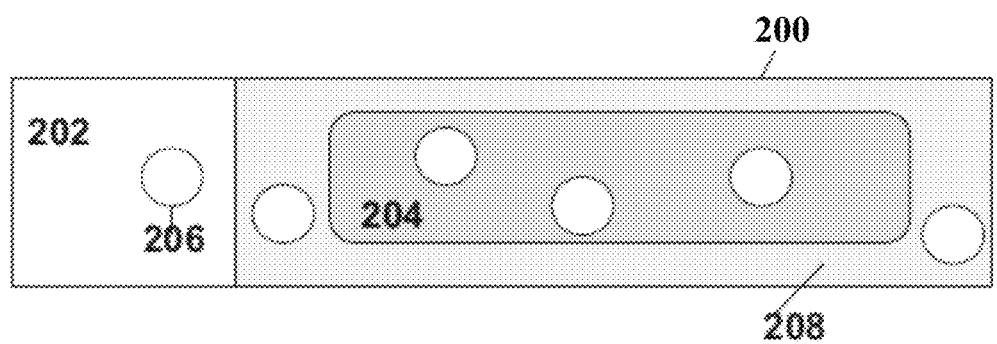
FIG. 2A shows an exemplary test strip for a single microbial volatile organic molecule according to one embodiment.

FIG. 2A illustrates an exemplary test strip 200 that may include a plastic substrate 202 coated with PDA 208. A portion of the PDA coated plastic substrate may be covered with MIP film 204. A sample solution 206 can be deposited on MIP film 204 and followed by washing sample solution. When a target molecule binds to the MIP film 204, the test strip may change, such as a color from blue to red, to indicate a "Yes" for the presence of the target. Otherwise, if no target molecule binds to the MIP film 204, there may be no change, such as no color change, which indicates "No" for the presence of the target.

Figure 2B:
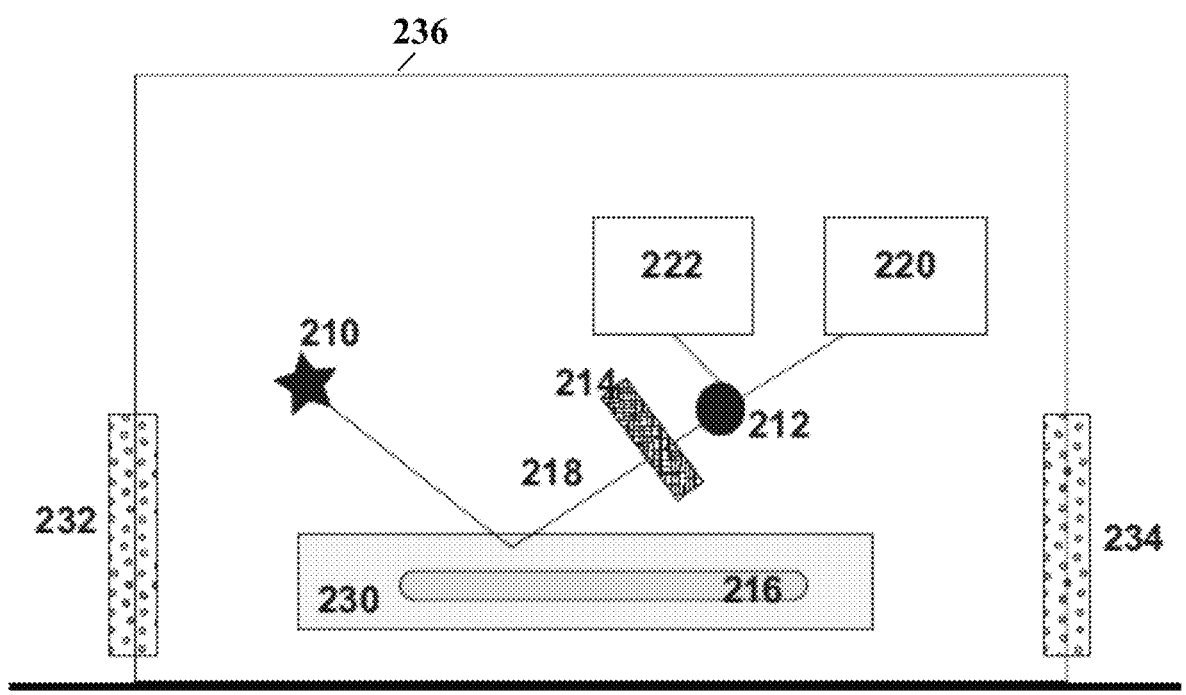
FIG. 2B shows an exemplary system with electronic reading of the sensing strips and local alarm plus wireless reporting of the results obtained as in FIG. 2A according to one embodiment.

FIG. 2B illustrates a system with electronic reading of the sensing strips and local alarm plus wireless reporting of the results obtained as described in FIG. 2A. The electronic reader may include one or more light emitting diodes 210 or other light sources and one or more detectors 212 to receive light reflected off the MIP. One or more filters 214 may admit only light reflected from the blue PDA 216. When the PDA, due to adsorption of the target into the MIP, changes color to blue, the reflected light signal 218 may diminish and/or disappear and a local alarm 220 may be triggered. Reflected light signal 218 may reflect off MIP 216 and/or PDA 208. Alternatively or in addition, a wireless signal 222 may be sent with a notification is sent to a remote location. The signal may be sent wirelessly or via any other data network. The notification may be one or more of an SMS message, MMS message, email, fax, phone call, etc. One or more airflow screens 232 may be provided to allow air into a housing 236. One or more fans 234 may be provided to draw air through the housing 236. In certain embodiments, both elements 232 and 234 may be screens or fans depending on the desired operation.

Figure 3:
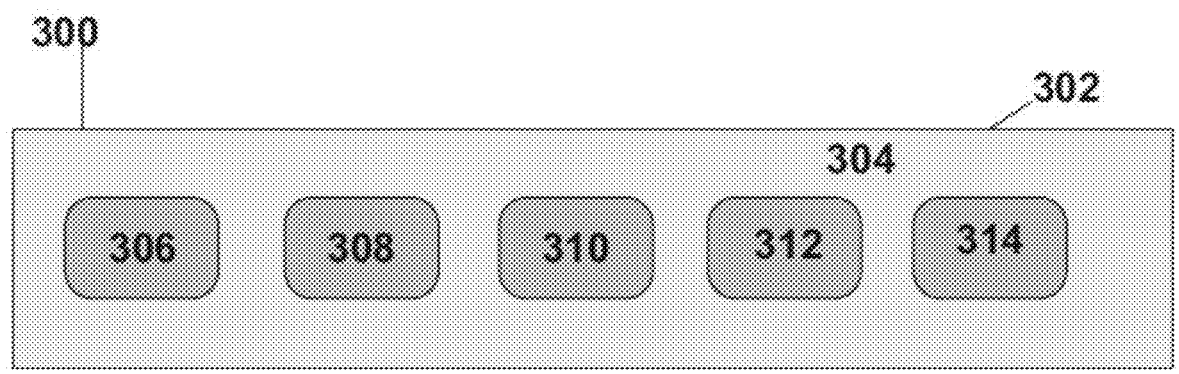
FIG. 3 illustrates an exemplary multicomponent test strip according to one embodiment.

FIG. 3 illustrates an exemplary multi-band test strip 300. The multi-band test strip 300 may include a plastic substrate 302 covered with a reporting PDA layer 304 isolated into five different regions. Each region may have a MIP solution 306, 308, 310, 312, 314 targeted to a different mVOC deposited onto the PDA reporting polymer. Alternatively, each region may be targeted to the same mVOC as a redundant test. If a particular target is present and is adsorbed by its respective MIP, the adsorption event may trigger a change in the strain of the PDA reporting layer, which may provide a color change to indicate the presence of the target. Otherwise, no color change may occur in each region.

One of the benefits of the methods disclosed herein over conventional methods for detection of the mVOCs may be molecular specificity. The sensor is passive, because the mVOCs may be adsorbed by the MIP film by exposure. There may be no need for the use of a pump or other moving parts for actively drawing air into the device although an additional embodiment may include, for example, a fan to draw air over the sensor.

Figure 4:
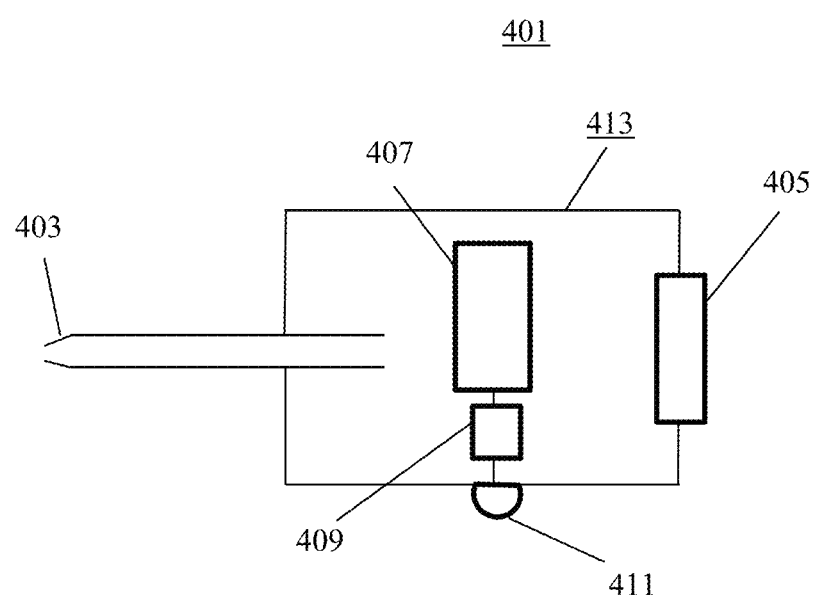
FIG. 4 shows an exemplary device for detecting mold behind a wall according to one embodiment.

FIG. 4 illustrates a system 401 for sampling for microbial growth behind a wall or other structural feature. An inlet 403 may pass through a structural element, such as a wall to sample air behind the structural element. For example, the inlet 403 may be passed through a sheetrock wall to sample air behind a finished side of a wall to check for mold or other microbial growth after a flood. The inlet 403 may be fluidly connected to a housing 413. The inlet 403 may be an air inlet. The housing 413 may contain one or more fans 405. The one or more fans may draw air through the inlet 403 and/or housing 413. One or more MIP sensors 407 may be located within the housing 413. The housing 413 may at least partially surround the one or more MIP sensors 407. The one or more sensors 407 may be in communication with one or more signal processors 409 for determining the presence or absence of mVOCs based on measurements of the one or more MIP sensors 407. The one or more signal processors 409 may output a result, such as to an indicator 411. The indicator 411 may be one or more LED lights, a display, etc. coupled to the housing 413. Alternatively, or in addition, the output may be provided to a remote system via a wireless or wired connection for further processing, alerting, reporting, etc.

Embodiments described herein may fill an unmet need, as there currently exists no passive sensor for the real-time detection of mVOCs. It will be appreciated by those skilled in the art that configuration, shape, and dimensions of the sensor can vary for particular applications.

Having described several embodiments, it will be recognized by those skilled in the art that various modifications, alternative constructions, and equivalents can be used without departing from the spirit of the disclosure. Accordingly, the above description should not be taken as limiting the scope of the disclosure. Those skilled in the art will appreciate that the presently disclosed instrumentalities teach by way of example and not by limitation. Therefore, the matter contained in the above description or shown in the accompanying drawings should be interpreted as illustrative and not in a limiting sense. The following claims are intended to cover all generic and specific features described herein. Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method for detecting one or more target molecules emitted from microbial sources, the method comprising:
providing a system comprising a molecularly imprinted polymer film including a polymer host with one or more binding sites for detection of one or more target molecules, wherein the one or more target molecules are airborne, the molecularly imprinted polymer film being formed by coating a liquid polymer solution, including the target molecule, onto a strain sensitive film configured to enable detection of the target molecule via a change of at least one of color, electrical resistance, and electrical conductivity in response to strain induced by binding of the target molecule to the one or more binding sites;
exposing said system to a gas, air sample, or vapor; and
measuring the change of said system, wherein said change is used to detect said one or more target molecules emitted from microbial sources in said gas, air sample, or vapor.

2. The method of claim 1, wherein the one or more target molecules are volatile organic molecules.

3. The method of claim 1, wherein the change is a color change upon detection of the one or more target molecules.

4. A method for producing a strain sensitive molecularly imprinted polymer film for detection of one or more target molecules emitted from microbial sources, the method comprising:
dissolving a polymer host comprising a structural component and a reporting component in a first solvent to form a first solution;
adding a target molecule to said first solution;
mixing said target molecule into said first solution to form a molecularly imprinted polymer solution;
coating said molecularly imprinted polymer solution onto a strain sensitive film to form molecularly imprinted polymer film including a polymer host with one or more binding sites for the target molecule, the target molecule being airborne, the strain sensitive film configured to enable detection of the target molecule via change of at least one of color, electrical resistance, and electrical conductivity in response to strain induced by binding of the target molecule to the one or more binding sites; and
removing the target molecule to form a strain sensitive molecularly imprinted polymer film.

5. The method of claim 4, wherein the coating comprises spin or dip coating.

6. The method of claim 4, wherein the removing the target molecule comprises:
extracting the target molecule from the strain sensitive molecularly imprinted polymer film using a second solvent,
wherein the polymer host is insoluble in the second solvent, and
wherein the target molecule is soluble in said second solvent.

7. The method of claim 4, wherein the first solvent has a boiling point lower than the boiling point of the target molecule, and wherein the removing the target molecule comprises evaporating the target molecule from the strain sensitive molecularly imprinted polymer film.

8. The method of claim 4, wherein the target molecule is selected from the group consisting of: 1,3-octadiene, 1-octen-3-ol, 2-butanol, 2-methylfuran, 3-methylfuran, anisole, and combinations thereof.

9. The method of claim 4, wherein the first solvent is selected from the group consisting of: alcohols, dimethylformamide, water, chloroform, and combinations thereof.

10. The method of claim 4, wherein the structural component is selected from the group consisting of: nylon-6, polyethyleneimine, polyurethane, polycarbonate, polymethylmethacrylate, polyvinylphenol, polyvinylpyrrolidinone, and combinations thereof.

11. The method of claim 4, wherein the strain sensitive film comprises polydiacetylene.

12. The method of claim 4, wherein the polymer host ranges from about 2 percent to about 15 percent by weight with respect to the first solvent in the first solution.

13. The method of claim 4, wherein the target molecule ranges from about 2 percent to about 10 percent by weight with respect to the first solvent in the molecularly imprinted polymer solution.

14. The method of claim 4, wherein the molecularly imprinted polymer solution comprises from about 2 to about 15 percent by weight of the structural component and the reporting component, and from about 2 to about 10 percent by weight of said target molecule.

15. The method of claim 4, wherein the strain sensitive molecularly imprinted polymer film composition comprises a molar ratio of about 1 to 1 of the structural component and the reporting component.

16. A system for detecting a target molecule, comprising:
a molecularly imprinted polymer film including a polymer host with one or more binding sites for the target molecule, the target molecule being airborne; and
a strain sensitive film in contact with the molecularly imprinted polymer film and configured to enable detection of the target molecule via change of at least one of color, electrical resistance, and electrical conductivity in response to strain induced by binding of the target molecule to the one or more binding sites;
the molecularly imprinted polymer film being formed by coating a liquid polymer solution, including the target molecule, onto the strain sensitive film.

17. The system of claim 16, further comprising a housing at least partially surrounding the molecularly imprinted polymer film, the housing forming an air inlet for conducting an air sample, including the target molecule, to the molecularly imprinted polymer film.

18. The system of claim 16, the molecularly imprinted polymer film being imprinted with the target molecule or a molecule homologous to the target molecule, wherein the target molecule is an airborne molecule selected from the group consisting of: 1,3-octadiene, 1-octen-3-ol, 2-butanol, 2-methylfuran, 3-methylfuran, anisole, and combinations thereof.

19. The system of claim 16, the molecularly imprinted polymer film being imprinted with the target molecule or a molecule homologous to the target molecule, wherein the target molecule is an airborne volatile organic molecule.

20. The system of claim 16, the strain sensitive film being configured to change color upon said binding of the target molecule.

21. The system of claim 16, wherein the strain sensitive film comprises polydiacetylene.

22. The system of claim 16, wherein the molecularly imprinted polymer film comprises antigens.

23. The system of claim 16, wherein the target molecule comprises 3-methylfuran.

24. The system of claim 16, further comprising:
one or more light emitting diodes configured to illuminate the molecularly imprinted polymer film; and
one or more detectors configured to receive light reflected off the molecularly imprinted polymer film to detect color change of the strain sensitive film.

25. The system of claim 16, configured to transmit, out of the system, a wireless signal in response to absorption of the target molecule by the molecularly imprinted polymer film.

26. The system of claim 16, thickness of the molecularly imprinted polymer film being between 1 and 500 nanometers.

27. The system of claim 16, further comprising a substrate, the strain sensitive film being coated onto the substrate, and the molecularly imprinted film being coated onto the strain sensitive film.

28. The system of claim 27, further comprising one or more additional molecularly imprinted polymer films coated onto different respective regions of the strain sensitive film, each of the molecularly imprinted film and the one or more additional molecularly imprinted polymer films including binding sites for different respective target molecules, to enable multiplexed detection of the different respective target molecules via the strain sensitive film.

29. A system for detecting target molecules, comprising:
two or more molecularly imprinted polymer films comprising a polymer host with one or more binding sites for different respective target molecules, the target molecules being airborne;
a strain sensitive film in contact with the one or more molecularly imprinted polymer films and configured to enable detection of target molecules via change of at least one of color, electrical resistance, and electrical conductivity in response to strain induced by binding of the target molecule to the one or more binding sites; and
a substrate, the strain sensitive film being coated onto the substrate, and the molecularly imprinted film being coated onto the strain sensitive film;
wherein the two or more molecularly imprinted polymer films are coated onto different respective regions of the strain sensitive film, to enable multiplexed detection of the different respective target molecules via the strain sensitive film.

* * * * *